United States Patent [19]

Kabbara

[11] Patent Number: 5,035,701
[45] Date of Patent: Jul. 30, 1991

[54] DEVICE AND METHOD TO CHECK THE TENSION OF A SUTURE DURING A SURGICAL OPERATION

[76] Inventor: Jamil Kabbara, 29 avenue Franklin Roosevelt, 75008 Paris, France

[21] Appl. No.: 451,307

[22] Filed: Dec. 15, 1989

[30] Foreign Application Priority Data

Dec. 26, 1988 [FR] France ................................ 8817180

[51] Int. Cl.⁵ ............................................ A61B 17/00
[52] U.S. Cl. ..................................... 606/148; 606/144
[58] Field of Search ........................ 606/139, 144–148, 606/150, 205, 206, 210, 32, 51, 52; 604/902

[56] References Cited

U.S. PATENT DOCUMENTS 4,927,428 5/1990 Richards ............................ 606/148
4,935,027 6/1990 Yoon .................................. 606/146

Primary Examiner—Robert A. Hafer
Assistant Examiner—Kerry Owens
Attorney, Agent, or Firm—Rines & Rines

[57] ABSTRACT

The invention concerns a device to check the tension of a suture during a surgical operation. A forceps comprises two jaws which can pivot on one another around an axis to tighten a suture and it can pivot around another axis almost perpendicular to the first. A spring whose force can be adjusted maintains it in one position in which it can be used as a conventional forceps, but if the pulling force applied to the suture exceeds a predetermined limit in a defined direction, the forceps pivot. According to another design, a piezoelectric element of a stress gauge is used to emit an information signal when the selected limit tension is exceeded.

13 Claims, 1 Drawing Sheet

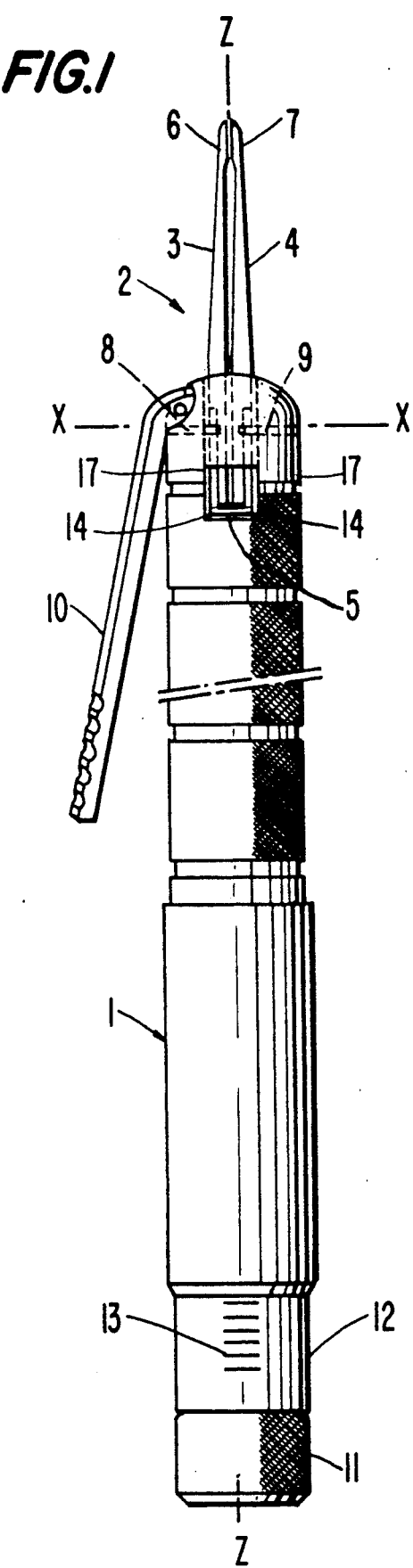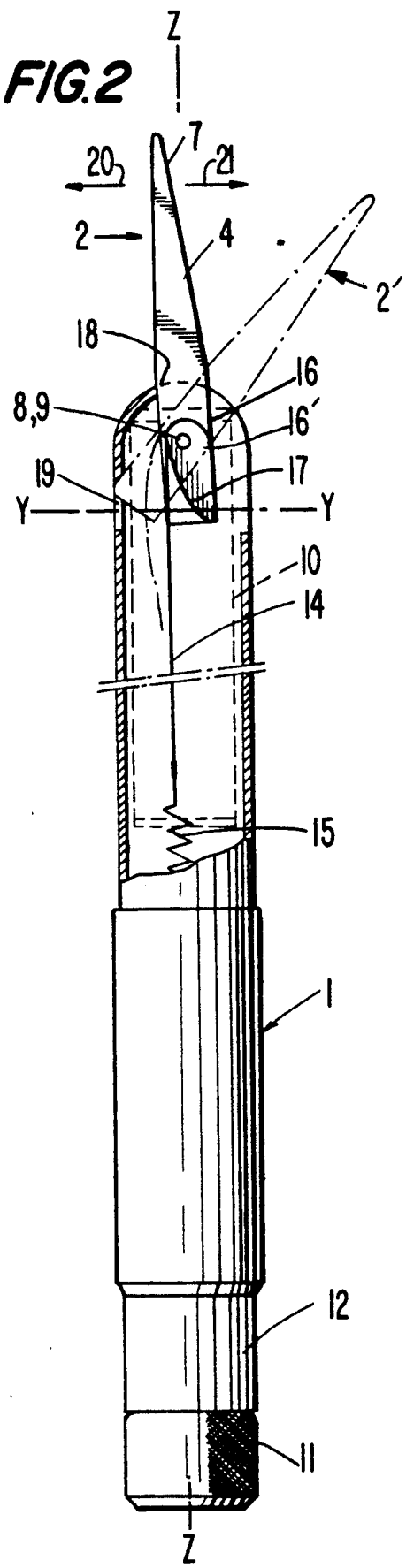

DEVICE AND METHOD TO CHECK THE TENSION OF A SUTURE DURING A SURGICAL OPERATION

The present invention concerns a device and method to check the tension of a suture during a surgical operation.

BACKGROUND

The tension must not significantly differ from one suture to another, but this does not mean that it must remain constant, it may vary, for example, between the extremities and the central zone of the suture line. Furthermore, the tension must be appropriate for the type of tissue concerned and the stress to which it is subjected. In practice, suturing depends primarily on the surgeon's dexterity, and requires great precision on his part in evaluating the force and execution of gestures.

The object of the present invention is to check the tension of each suture in order to achieve as even a tension as possible throughout the sutures in view of obtaining the most "natural" wound closure, to promote wound healing and to minimize postoperative complications arising from uneven tension due to excessive tightening or slack such as: astygmatism, embolism, oozing of wounds, etc.

Document EP-A-0115624 describes a device designed to measure the tension of skin fragments during surgery, but it has proven unsuitable for the practical checking of suture tension during an operation.

OBJECTS AND SUMMARY

The present invention is designed to supply and has as an object a device and method utilizable by the surgeon during an operation, and which also allows him to handle the suture before actually checking the tension.

To achieve this result, in summary, the invention consists in a device to check the tension of a suture during a surgical operation, comprising a body, a gripping device to catch hold of the suture, means to actuate the gripping device, and means to signal that the stress, resulting from the displacement of the body by the surgeon and the resistance opposed to such displacement by the tension of the suture held in the gripping device, exceeds a predetermined level, characterized by the fact that the gripping device is mounted on a pivot with respect to the body and that a elastic return means prevents the gripping device from pivoting provided the suture tension does not exceed a predetermined level.

An advantage is that the gripping device can only pivot in one direction, and that pivoting in the other direction is prevented by a stop.

Preferably, the gripping device is a forceps comprising two jaws which can pivot one on the other around an axis which is almost perpendicular to the pivoting axis of the gripping device with respect to the body.

Preferably also, the elastic return means consists in a traction spring or enclosure filled with gas and closed by a mobile plunger. The force of this elastic return means can be adjusted and the means itself is connected to the gripping means by a connecting device, such as a cable, resting on the said gripping device at a point displaced from the pivoting axis with respect to the body.

According to another design, the gripping device is substantially or almost fixed with respect to the body, and the means indicating that the stress exceeds the predetermined level consists of a piezo-electric element or other stress gauge element, and means to produce an information indication signal in response to signals emitted by this element.

These two designs have in common the fact that certain movements are possible, and notably traction along the axis of the body, without causing the relative displacement of the gripping device with respect to the body and in both instances, indications are provided to the surgeon of excessive suture tension.

DRAWINGS

The invention will now be described in greater detail using a practical, non-exhaustive, example, illustrated with drawings, among which:

FIG. 1 is a side view of a device according to the invention, and

FIG. 2 is a side view, taken at 90° with respect to the orientation of FIG. 1, and a partial section, of the same device.

INVENTION

The illustrated device comprises a longitudinal tubular body 1, of suitable dimensions for correct gripping by the surgeon. At one of its extremities is attached a forceps 2, consisting of a single piece cut to make two jaws 3, 4, connected by a relatively flexible part 5, equivalent to a Y-Y axis articulation. Extremities 6, 7 of the jaws, are classically shaped to allow correct gripping of a suture.

The forceps 2 is mounted on the body 1 by two transverse pivots 8, 9, perpendicular to the longitudinal Z-Z axis of the body 1, and extending towards one another. One of the pivots 8 is fixed, the other pivot 9, can slide in a bore, by the action of a lever 10. The position of the X-X transverse axis of pivots 8, 9 is located between the flexible part 5 of the forceps and extremities 6, 7 of the jaws, such that actuating lever 10 tightens the jaws 3, 4, and grips a suture between 6, 7, if a suture is present.

The opposite end of the body 1 bears a milled knob 11, which is part of a screw system 12, which can be displaced axially (Z-Z) with respect to the body 1. A graduated scale 13 allows the position of the screw system 12 to be precisely adjusted.

If one now considers FIG. 2, one can see that the forceps 2 is shown in one position, in which it is approximately situated along the longitudinal Z-Z axis of the body 1, and in a second position, in which it is at a distance from this axis, with pivoting occurring around the transverse X-X axis of FIG. 1, which passes through pivots 8 and 9. A flexible cable 14 is connected to the screw system 12 through an elastic or resilient traction spring 15. It is also attached to forceps 2 at an anchoring point 16, displaced from or off the axis with respect to pivot 8. The outside surface of the forceps comprises a raised part 17, with an arc-shaped edge on which rests or rides the cable 14. In the resting position, shown in solid lines, in which forceps 2 lies along the axis Z-Z of the body 1, the cable 14 maintains the forces pressed against a stop 18, formed by the edge of an opening made in the top wall of the body 1.

In the position shown in broken lines, in which the forceps lie in position 2', they press against another stop 19, consisting of the edge of another opening made in the side wall of the body. The angle formed by the two limit positions 2, 2' of the forceps is approximately 45°. The limit position 2' corresponds to a frank excess beyond the return force of spring 15, exerted by cable 14. In this position, the anchoring point of cable 14 moves to 16', but because of the arc-shape of the circle of edge 17, the point of application of the force of spring 15 is almost at the same distance from the X-X pivoting axis.

The operating procedure is easy to imagine: before operating, the surgeon adjusts the return force of spring 15 using the milled piece 11, i.e. he adjusts the maximum or limit tension of the suture according to the planned operation. He can then use his forceps as a conventional forceps-needle holder, provided the traction on the suture is exerted along the direction indicated by arrow 20, i.e., towards the left of FIG. 2. If he wants to check the tension of the suture, all he need do is pull on the suture in the opposite direction indicated by arrow 21; i.e. towards the right of FIG. 2. If the tension of this suture is excessive, the forceps will flex or rotate about axis X-X and will tend to change from position 2 to position 2'; this is readily observably indicated, even under a microscope, if microsurgery is being performed. If the surgeon turns the device in his hand halfway around the Z-Z axis of the body, the traction to check the suture will occur in the same direction as the direction of suturing. Further modifications will occur to those skilled in this art, such being considered to fall within the spirit and scope of the invention as defined in the appended claims.

What is claimed is:

1. Device to check the tension of a suture during a surgical operation, comprising a body (1), a gripping device (2, 3, 4) appropriate for gripping a suture, means (9, 10) to actuate the gripping device, and a means to signal that the stress resulting from the displacement of the body by the surgeon and the resistance opposed to this displacement by the tension of the suture held by the gripping device, exceeds a predetermined level;

and wherein the gripping device is mounted such that it pivots with respect to the body, and an elastic return means prevents the gripping device from pivoting provided the tension of the suture does not exceed said predetermined level.

2. Device according to claim 1, in which the gripping means is a forceps (2) comprising two jaws (3, 4) which can pivot on one another around an axis (Y-Y) almost perpendicular to the pivoting axis (X-X) of the gripping means with respect to the body.

3. Device according to claim 1 in which the force of this elastic return means is adjustable and connected to the gripping device by a connecting means (14) resting on the said gripping device on a point 16 displaced from its pivoting axis (X-X) with respect to the body.

4. Device to check the tension of a suture during a surgical operation, comprising a body (1), a gripping device (2, 3, 4) appropriate for gripping the suture, means (9, 10) to activate the gripping device, and a means to signal that the stress, which results from the displacement of the body by the surgeon and from the resistance opposed to this displacement by the tension of the suture held by the gripping device, exceeds a predetermined level, and wherein the gripping device is substantially fixed with respect to the body, and the means to signal that the stress exceeds the predetermined level includes a stress gauge element, and the device having means to emit an information signal in response to the signals emitted by this element.

5. Device according to claim 2 and in which the suture stress signal means comprises the observable extent of the jaw pivoting.

6. Device according to claim 1 and in which the suture stress signal means comprises a stress gauge such as a piezoelectric element.

7. A method of checking and controlling the tension of a suture during a surgical operation with longitudinally extending forceps the jaws of which pivot along a first transverse axis to grip a suture and are also pivotable around a second transverse axis substantially perpendicular to the first axis, the method comprising, gripping a suture by closing the forcep jaws thereupon and commencing suturing with traction exerted along a suturing direction; predetermining a desired suture tension or stress limit; checking suture tension by pulling on the suture in the opposite direction; indicating suture tension excessive of the predetermined desired tension limit by the flexing or rotating of the forceps about said second transverse axis; and lessening the tension of the suturing below said limit.

8. A method as claimed in claim 7 and in which the suture tension predetermining is effected by applying elastically controlled tension to the forceps sufficient to resist flexing or rotating about said second transverse axis until the tension of the suture exceeds the predetermined desired tension limit.

9. A method as claimed in claim 7 and in which said excessive suture tension indicating is effected by a stress gauge emitting a signal when the excessive tension occurs.

10. A method as claimed in claim 7 and in which the forceps is rotated half-way around its longitudinal axis perpendicular to both the first and second transverse axes such that the said opposite direction becomes aligned with the suturing direction.

11. A device for checking the tension of a suture during a surgical operation having, in combination, longitudinally extending forceps provided with a pair of jaws pivotable along a transverse first axis to grip a suture, and also pivotable about a second transverse axis substantially perpendicular to the first axis; elastic tensioning means connected with the forceps to maintain the same in a predetermined use position; and means for adjusting the tension of the elastic tensioning means in accordance with a desired predetermined suture tension limit and responsive to a pulling force applied to the suture during suturing that exceeds said limit, for causing flexing or rotating of the jaws to a different position about said second transverse axis, indicative of the excessive suture tension.

12. A device as claimed in claim 11 and in which said tensioning means is disposed along a longitudinally extending body orthogonal to both the first and second transverse axes and carrying the forceps at one end, and provided with tension adjusting means near the opposite end.

13. A device as claimed in claim 12 and in which said forcep jaws are provided below their pivot with arcuate edges to which the tensioning means is connected to control flexing or rotating along the said second axis in response to the reaching of excessive suture tension, stop means being provided for holding the forceps in the said use position in the absence of excessive suture tension.

* * * * *